United States Patent [19]

Leston

[11] 4,429,169

[45] Jan. 31, 1984

[54] PROCESS FOR SEPARATING ISOPROPYLATED M-CRESOLS

[75] Inventor: Gerd Leston, Pittsburgh, Pa.

[73] Assignee: Koppers Company, Inc., Pittsburgh, Pa.

[21] Appl. No.: 372,055

[22] Filed: Apr. 26, 1982

[51] Int. Cl.$^3$ .............................................. C07C 37/68
[52] U.S. Cl. .................................... 568/756; 568/749; 568/750; 568/751; 568/781
[58] Field of Search ............... 568/749, 750, 751, 756, 568/781

[56] References Cited

U.S. PATENT DOCUMENTS

| | | | |
|---|---|---|---|
| 4,267,389 | 5/1981 | Leston | 568/750 |
| 4,267,390 | 5/1981 | Leston | 568/750 |
| 4,267,391 | 5/1981 | Leston | 568/750 |
| 4,267,392 | 5/1981 | Leston | 568/750 |

FOREIGN PATENT DOCUMENTS 1125944  3/1962  Fed. Rep. of Germany ...... 568/756

OTHER PUBLICATIONS

Sharpless, "J. Org. Chem.", vol. 40 (1975), pp. 1252–1257.

*Primary Examiner*—Werren B. Lone
*Attorney, Agent, or Firm*—J. Timothy Keane; Daniel J. Long; Herbert J. Zeh, Jr.

[57] ABSTRACT

A process is disclosed for separating 5-isopropyl-m-cresol from other isopropylated m-cresols by treating a mixture of the isopropylated m-cresols with a metal halide salt. The metal halide salt preferentially forms a complex with 5-isopropyl-m-cresol over other related closely-boiling isopropylated m-cresols in the mixture. The preferentially-formed complex of 5-isopropyl-m-cresol may then be isolated from the mixture and the complex decomposed to provide a product substantially enriched in, or substantially entirely composed of, 5-isopropyl-m-cresol. The process is particularly suitable for isolating 5-isopropyl-m-cresol from closely-boiling isomers, and diisopropylated m-cresols.

6 Claims, No Drawings

PROCESS FOR SEPARATING ISOPROPYLATED M-CRESOLS

BACKGROUND OF THE INVENTION

1. Field of the Invention

Preferential complexation of one organic compound in a mixture of related compounds is a known technique for resolving mixtures of compounds having close boiling points. Of particular interest herein is a method for isolating 5-isopropyl-m-cresol by preferential complexation of this compound from a mixture of close-boiling isomers and di-isopropylated m-cresols.

2. State of the Art

Mixtures of isopropylated m-cresols are available as end-products or by-products from the acid-catalyzed isopropylation of m-cresol to make mixed isopropylated m-cresols. Such reactions produce many closely-boiling isopropylated m-cresols such as 6-isopropyl-m-cresol, commonly known as thymol, a pharmaceutical; 5-isopropyl-m-cresol, also known as 5-thymol or sym-thymol or m-thymol, a pesticide intermediate; and 4-isopropyl-m-cresol, also known as p-thymol; and 2-isopropyl-m-cresol, also known as 2-thymol. In the isopropylation of m-cresol to make one or more desirable isomers, a mixture of isomeric mono- and di-isopropylated m-cresols is usually produced. The isolation and purification of individual isopropylated m-cresols are very difficult by the use of conventional separation methods such as fractional distillation.

There are chemical processes known for separating closely-boiling organic compounds by methods other than or in addition to, energy-intensive physical separation techniques such as fractional distillation or fractional crystallization. These chemical processes involve a step of preferential complexation of one component of a mixture of closely-boiling compounds over other components of the mixture. For example, U.S. Pat. No. 4,267,389 to Leston, describes treating a phenolic mixture comprising para-cresol, methylated phenols and ethylated phenols, with an inorganic metal halide salt, such as calcium bromide, to remove para-cresol from the mixture. Removal of para-cresol from the mixture involves formation of a complex between para-cresol and calcium bromide, which complex forms preferentially over complexes between calcium bromide and other components of the phenolic mixture.

Mixtures of various alcohols may be resolved by treatment with a metal halide salt. For example, in Sharpless et al., J. Org. Chem., Vol. 40, No. 9, pp. 1252–1257 (1975) there is reported a study of competition between pairs of mono-hydroxy alcohols and mono-hydroxy phenols for complex formation with a metal halide salt. This study finds that phenols as a class form poorer complexes than alcohols of comparable melting points, probably because the phenols are weaker bases than the comparable alcohols.

There remains need, therefore, for methods for the isolation of 5-isopropyl-m-cresol from a mixture of closely-boiling isopropylated m-cresols by chemical complexation methods, rather than by fractional crystallization or distillation.

SUMMARY OF THE INVENTION

Separation of 5-isopropyl-m-cresol from a mixture of two or more isopropylated m-cresols may be accomplished by a process involving a step of forming a solid complex preferentially between a metal halide salt and 5-isopropyl-m-cresol in the mixture. A metal halide salt suitable for forming the solid complex may be selected from the group consisting of calcium bromide, calcium chloride, lithium bromide, magnesium chloride and magnesium bromide.

The method involves bringing together a mixture of two or more isopropylated m-cresols and a selected metal halide salt, the metal halide being selected such that a complex forms with 5-isopropyl-m-cresol in preference to, or preferentially over, other isopropylated m-cresols in the mixture. This preferentially formed complex constitutes a solid material in contact with a liquid phase such as may be provided by aliphatic, alicyclic and aromatic hydrocarbons, and their chlorinated derivatives, ethers, esters and ketones. Also, any combination of such solvents may be used. Alcohols are specifically excluded as solvents inasmuch as they form complexes with the metal halide salt. The solid complex may then be removed or isolated from the liquid phase and thereafter decomposed to a product comprising a predominantly greater amount of the preferentially-complexed m-thymol than other isopropylated m-cresols as compared to the relative amounts of isopropylated m-cresols derived from complexes which form with the selected metal halide salt, but in lesser amount than the amount of m-thymol derived from the preferentially-formed complex.

One advantage provided by the process of the invention is that good separation of m-thymol can be obtained from a mixture of two or more isopropylated m-cresols which have boiling points in a relatively narrow range, 5°–15° C., which separation would be substantially impossible to accomplish in a one-stage fractional distillation or crystallization. A second advantage resides in this chemical-separation process requiring significantly less energy to accomplish good resolution of closely-boiling isopropylated m-cresols than physical-separation methods such as fractional distillation or crystallization.

The chemical-separation process of the invention may also be used advantageously in conjunction with conventional physical-separation processes. For example, calcium bromide complexation may be used in an initial treatment of an isopropylated m-cresol mixture for separating the closest-boiling compounds, that is, compounds boiling within a range of five to ten centigrade degrees. Then, a resulting mixture of compounds having boiling points differing by more than five centigrade degrees can be treated by distillation or crystallization for more complete resolution of the mixture.

The term "isomeric isopropylated m-cresols" means two or more isopropylated m-cresols wherein the isopropyl groups are in different positions from each other. The phrases "resolving a mixture of isopropylated m-cresols" and "resolution of a mixture of isopropylated m-cresols" relate to a mechanism or a result in which the individual components of a mixture containing two or more isopropylated m-cresols may be separated or isolated from each other. Thus, the separation of a significant amount of one isopropylated m-cresol from a mixture of two isopropylated m-cresols constitutes a resolution of the mixture. The phrases also embrace separation of a multi-component mixture into groups of isopropylated m-cresols, each group containing two or more isopropylated m-cresols. Also included within the definition are treatments resulting in a significant increase in the amount of 5-isopropyl-m-cresol as compared to the composition of the original mixture of isopropylated m-cresols, even where the original mixture contained relatively small amounts of the enriched isopropylated m-cresol. It is contemplated that a differentiation or enrichment in the relative amounts of isopropylated m-cresol is a "significant enrichment" if treatment of a mixture provides an increase of at least about 20 weight percent in one or more of the isopropylated m-cresols as compared to the composition of the original mixture.

The phrases "preferentially-formed complex" and "predominantly-complexed phenolic" are intended as abbreviated description of the complex, comprising a selected metal halide salt and m-thymol which forms in an amount significantly greater than an amount of any other complex of another isopropylated m-cresol resulting from treatment of the isopropylated m-cresol mixture with the selected metal halide salt. Any complex formed will preferably be comprised substantially entirely of a complex of 5-isopropyl-m-cresol. It is recognized, however, that other isopropylated m-cresols in a starting mixture may form complexes with the selected salt in secondary or lesser amounts than the primary, predominantly-formed complex. Such secondary complex formation in lesser amounts is not deleterious provided that the ratio of the predominant complex to the secondary complex in the resulting solid material is sufficiently high to provide a useful resolution of an isopropylated m-cresol mixture. It is contemplated that a primary/secondary or predominant/lesser ratio of the relative amounts of complexes of the treated mixture constitutes a significant and usefully-resolved mixture of isopropylated m-cresols.

Mixtures of isopropylated m-cresols susceptible to treatment with the process of the invention include mixtures of two or more isopropylated m-cresols such as 2-isopropyl-m-cresol, 4-isopropyl-m-cresol, 5-isopropyl-m-cresol, 6-isopropyl-m-cresol, 2,4-diisopropyl-m-cresol, 2,6-diisopropyl-m-cresol, 4,6-diisopropyl-m-cresol and 2,5-diisopropyl-m-cresol.

The family of metal halide salts which may be used in the invention are characterized in having several features in common. For example, in addition to each member of the family being an inorganic salt of a metallic chloride or bromide, these halide salts are characterized in taking on water of hydration. The hydratable nature of these metal halide salts is believed to be significant in the mechanism of complex formation with the phenolics, even though no water is involved in the complexation reaction. Of the family of metal halide salts suitable for use in the invention, calcium bromide is preferred. It is also preferred, whether calcium bromide or calcium chloride or any other of the halide salts is used, that the salt have a water content, either as hydrate or occluded, of less than about ten weight percent. Also, it is preferred that the salt have a particle size less than about 200 mesh.

Solvents which may be used in the complexation reaction include those organic compounds which dissolve the phenolic mixtures but do not preferentially react with the metal halide salt. Solvents suitable include aliphatic, alicyclic and aromatic hydrocarbons, their chlorinated derivatives, ethers, esters and ketones. Alcohols are specifically excluded since they may form complexes with the metal halide salt. Mixtures of solvents may also be used.

The process of the invention is particularly suitable for resolving mixtures of close-boiling isopropylated m-cresols. Examples of such mixtures include the following: 5-isopropyl-m-cresol and 4-isopropyl-m-cresol; 5-isopropyl-m-cresol and 6-isopropyl-m-cresol; 5-isopropyl-m-cresol and 2,6-diisopropyl-m-cresol; 5-isopropyl-m-cresol and 2-isopropyl-m-cresol.

Generally, the metal halide salt is added to the mixture of phenolics dissolved in, or in contact with, a solvent. For calcium bromide, for example, the salt is preferably added in amount in a range from about 0.1 mole to about 4 moles to one mole of the 5-isopropyl-m-cresol to be preferentially complexed. Usually, the complexation reaction takes place in the presence of a catalyst such as a lower aliphatic alcohol. A typical catalytic amount of the alcohol would be approximately five mole percent of the alcohol based on the total isopropylated m-cresol content.

After the aforementioned components are brought together as a mixture, usually in the form of a slurry, the mixture is agitated for a period of time sufficient for the 5-thymol-metal halide salt complex to form. A typical mixing time is in a range from about one hour to about 24 hours. Mixing is typically conducted at room temperature and at atmospheric pressure, although the complexation reaction may be conducted at practically any temperature in a range from about 0° C. to about 150° C. Superatmospheric pressure may be used to avoid loss of reactants and solvents. Also, care must be taken to exclude ambient moisture from the reaction mixture.

After the mixing period, the mixture contains a fluffy white or gray solid material component in contact with a liquid component. The solid material may be separated from the liquid component by any conventional separation techniques such as by decanting, by centrifugation, or by filtration. If filtration is used to separate the solid material from the liquid, the filtration may be conducted with the aid of pressure gradient applied across the filter medium. The separated solid material may be washed with small portions of solvent, and the washings thereafter may be combined with the filtrate. After the washing step, the separated solid material may be optionally dried, usually by means of low heat or in a desiccator under reduced pressure. The drying step is carried out until the solid material reaches a constant weight.

The solid material, which contains the 5-isopropyl-m-cresol-metal halide salt complex, is then decomposed to provide the desired m-thymol. Decomposition may be accomplished by hydrolysis of the complex in water, by heating the complex at a temperature usually in a range of from about 150° C. to about 350° C., or by treatment with an alcohol, such as a lower boiling aliphatic alcohol. Preferred decomposition methods include water hydrolysis and heat treatment of the complex. In decomposition of the complex by water hydrolysis, the phenolic may be recovered by treating the water with an organic solvent, typically ether. In decomposition of the complex with heat, separation of the m-thymol from the halide salt residue may be performed by distillation, filtration or centrifugation. In either of these decomposition methods, the metal halide salt may be recovered and recycled for treatment of another mixture of isopropylated m-cresols, or for subsequent treatment of the separated isopropylated m-cresols in the event of incomplete separation of the mixture of isopropylated m-cresols.

It is an important feature of the invention that the liquid portion of the mixture treated with the metal halide salt contains the phenolics which less predominantly form complexes with the metal halide salt or which form substantially no complexes with the metal halide salt. Thus the liquid portion of the treated mixture will be enriched in these isopropylated m-cresols and depleted in the m-thymol which predominantly complexes with calcium bromide. These isopropylated m-cresols may be recovered from this liquid portion by conventional distillation or fractionation techniques.

In order to demonstrate the invention, a mixture of isopropylated m-cresols was treated with calcium bromide to show the formation of a m-thymol-CaBr$_2$ complex, as described in Example I and Table I.

EXAMPLE I

A reaction vessel equipped with stirring means was charged with 7.5 g isopropylated m-cresols (50 mmole) along with about 0.2 ml absolute ethanol and 25 ml hexane as a solvent for the isopropylated m-cresols to form a solution. To the reaction vessel, there was added 10.0 g finely-ground anhydrous CaBr$_2$ (50 mmole) to form a slurry-like mixture. The reaction vessel was equipped with a drying tube filled with a desiccant, such as anhydrous calcium sulfate, for the purpose of excluding atmospheric moisture from the reaction mixture during the reaction. The mixture was stirred about 15 hours at room temperature after which time there was observed a large amount of a fluffy, white solid material suspended in the liquid solution. Then the mixture was filtered under suction, in a manner to minimize exposure of the mixture to ambient moisture, to separate the fluffy solid material from the liquid component. The separated solid was washed twice with 10 ml portions of hexane, the washings then combined with the filtrate. The washed solid was dried in a desiccator under a pressure of 1 mm Hg absolute for two hours at room temperature. The dried solid amounted to 14.94 g, a portion of which was hydrolyzed in water to form a hydrolyzate, which hydrolyzate was extracted from the water by five sequential treatments of the water containing the hydrolyzate with hexane. GC analysis the hexane extract derived from the precipitate showed that the solid material contained substantially entirely a complex of m-thymol and calcium bromide. Analyses of the filtrate and of the starting mixture are shown in Table I.

TABLE 1

| | GC Analyses, Area Percent | | |
|---|---|---|---|
| | Starting Material | Complex | Filtrate |
| m-cresol | .33 | .17 | .50 |
| 2-thymol | .29 | .18 | 1.05 |
| 6-thymol | 1.54 | .50 | 3.89 |
| unknown | .53 | .48 | .82 |
| m-thymol | 85.70 | 96.45 | 65.05 |
| 4-thymol | 9.26 | .13 | 21.89 |

TABLE 1-continued

| | GC Analyses, Area Percent | | |
|---|---|---|---|
| | Starting Material | Complex | Filtrate |
| 4,6-diisopropyl-m-cresol | 2.35 | .92 | 6.80 |

What is claimed is:

1. A process for resolving a mixture of two or more isopropylated m-cresols, one of which is m-thymol, comprising the step of:

treating a mixture of two or more closely-boiling isopropylated m-cresols, one of which is m-thymol, said mixture having a temperature in a range from about 0° C. to about 150° C., with a metal halide salt selected from the group consisting of calcium bromide, calcium chloride, lithium bromide, magnesium chloride and magnesium bromide, so as to form preferentially a complex comprised of the selected metal halide salt and m-thymol, whereby the preferentially-formed metal halide salt m-thymol complex may be isolated and thereafter decomposed to a product comprising a predominantly greater amount of m-thymol over other isopropylated m-cresols present, as compared to the relative amount of m-thymol present in the original mixture of isopropylated m-cresols.

2. The process of claim 1 wherein one of the isopropylated m-cresols in the mixture is m-thymol and another isopropylated m-cresol is a closely-boiling isomer.

3. The process of claim 1 wherein the mixture contains two isopropylated m-cresols, the first isopropylated m-cresol being m-thymol and the second isopropylated m-cresol being a closely-boiling diisopropylated m-cresol.

4. The process of claim 1 wherein said selected metal halide salt is calcium bromide.

5. The process of claim 4 wherein the molar ratio of meta-thymol:calcium bromide in the starting mixture is in a range from about 0.2:1 to about 5.0:1.0.

6. A process for resolving a mixture of two or more isopropylated m-cresols, one of said m-cresols being 4-thymol and another of said m-cresols being m-thymol, comprising the step of:

treating a mixture of two or more isopropylated m-cresols, one of said m-cresols being 4-thymol and another of said m-cresols being m-thymol, said mixture having a temperature in a range from about 0° C. to about 150° C., with a metal halide salt selected from the group consisting of calcium bromide, calcium chloride, lithium bromide, magnesium chloride and magnesium bromide, so as to form preferentially a complex of the selected metal halide salt and m-thymol, whereby the preferentially-formed metal halide m-thymol complex may be isolated and thereafter decomposed to a product comprising a predominantly greater amount of m-thymol over other isopropylated m-cresols present, as compared to the relative amount of m-thymol present in the original mixture of isopropylated m-cresols.

* * * * *